(12) United States Patent
Nishida et al.

(10) Patent No.: US 11,931,435 B2
(45) Date of Patent: Mar. 19, 2024

(54) WATER-IN-OIL TYPE EMULSIFIED COSMETIC

(71) Applicant: SHISEIDO COMPANY, LTD., Tokyo (JP)

(72) Inventors: Keita Nishida, Yokohama (JP); Satoshi Yamaki, Yokohama (JP); Shoji Tajima, Yokohama (JP); Hideto Ueda, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/095,457

(22) PCT Filed: Apr. 12, 2017

(86) PCT No.: PCT/JP2017/014935
§ 371 (c)(1),
(2) Date: Oct. 22, 2018

(87) PCT Pub. No.: WO2017/187977
PCT Pub. Date: Nov. 2, 2017

(65) Prior Publication Data
US 2019/0117531 A1 Apr. 25, 2019

(30) Foreign Application Priority Data
Apr. 28, 2016 (JP) ................. 2016-091449

(51) Int. Cl.
| A61Q 17/04 | (2006.01) |
|---|---|
| A61K 8/02 | (2006.01) |
| A61K 8/06 | (2006.01) |
| A61K 8/25 | (2006.01) |
| A61K 8/27 | (2006.01) |
| A61K 8/29 | (2006.01) |
| A61K 8/30 | (2006.01) |
| A61K 8/36 | (2006.01) |
| A61K 8/37 | (2006.01) |
| A61K 8/41 | (2006.01) |
| A61K 8/60 | (2006.01) |
| A61K 8/73 | (2006.01) |
| A61K 8/86 | (2006.01) |
| A61K 8/89 | (2006.01) |
| A61K 8/891 | (2006.01) |
| A61K 8/893 | (2006.01) |
| A61K 8/92 | (2006.01) |
| A61Q 1/00 | (2006.01) |
| A61Q 1/02 | (2006.01) |
| A61Q 5/06 | (2006.01) |
| A61Q 19/00 | (2006.01) |

(52) U.S. Cl.
CPC ............ *A61K 8/064* (2013.01); *A61K 8/0241* (2013.01); *A61K 8/06* (2013.01); *A61K 8/25* (2013.01); *A61K 8/27* (2013.01); *A61K 8/29* (2013.01); *A61K 8/30* (2013.01); *A61K 8/36* (2013.01); *A61K 8/37* (2013.01); *A61K 8/416* (2013.01); *A61K 8/60* (2013.01); *A61K 8/73* (2013.01); *A61K 8/732* (2013.01); *A61K 8/86* (2013.01); *A61K 8/89* (2013.01); *A61K 8/891* (2013.01); *A61K 8/893* (2013.01); *A61K 8/922* (2013.01); *A61Q 1/00* (2013.01); *A61Q 1/02* (2013.01); *A61Q 5/06* (2013.01); *A61Q 17/04* (2013.01); *A61Q 19/00* (2013.01); *A61K 2800/42* (2013.01); *A61K 2800/48* (2013.01)

(58) Field of Classification Search
CPC ...... A61K 8/064; A61K 8/0241; A61K 8/416; A61K 8/60; A61K 8/732; A61K 8/89; A61K 8/922; A61K 2800/42; A61K 2800/48; A61Q 1/02; A61Q 17/04
See application file for complete search history.

(56) References Cited

U.S. PATENT DOCUMENTS

| 2006/0188463 A1* | 8/2006 | Kim ................. A61K 8/738 424/70.13 |
| 2010/0166684 A1* | 7/2010 | Kokeguchi ............ A61K 8/37 424/59 |

(Continued)

FOREIGN PATENT DOCUMENTS

| EP | 3 213 742 A1 | 9/2017 |
| JP | A-HEI 1180237 | 7/1989 |

(Continued)

OTHER PUBLICATIONS

English machine translation of WO 2012/121309 A1 made Dec. 28, 2020. (Year: 2020).*
PCT/JP2017/014935 International Search Report and Written Opinion, dated Jul. 4, 2017, 3 pages—English, 10 pages—Japanese.
PCT/JP2015/080764, International Search Report and Written Opinion, dated Feb. 2, 2016, 3 pages—English, 9 pages—Japanese.
Ishii, Hiroaki, et al., Efficacy and Physical Properties of Sunscreen Film, Oleoscience, 2009, vol. 9, No. 5, p. 183-188, ISSN: 1345-8949.
U.S. Appl. No. 15/765,012 dated Apr. 17, 2019, 12 pages.
U.S. Appl. No. 15/522,016 Office Action dated Mar. 25, 2019, 13 pages.

(Continued)

*Primary Examiner* — Michael B. Pallay
(74) *Attorney, Agent, or Firm* — Andrew F. Young; Nolte Lackenbach Siegel

(57) ABSTRACT

A water-in-oil type emulsified cosmetic has an unprecedented property wherein, by coming into contact with perspiration or water, the color development and the color uniformity are improved over the conditions immediately after application. The water-in-oil type emulsified cosmetic includes: (A) an organically modified clay mineral; (B) an oil phase thickener other than the (A) organically modified clay mineral; (C) a non-volatile liquid oil other than a silicone oil; (D) a silicone-based surfactant having an HLB of less than 8; and (E) a colorant; wherein a weight ratio defined by [(A)+(B)]/(C) is at least 0.04 and less than 0.68.

4 Claims, No Drawings

(56) References Cited

U.S. PATENT DOCUMENTS

| | | | |
|---|---|---|---|
| 2012/0196942 A1* | 8/2012 | Yamaguchi | A61K 8/0295 |
| | | | 514/784 |
| 2012/0201905 A1 | 8/2012 | Mune et al. | |
| 2012/0269875 A1* | 10/2012 | Tamura | A61K 8/022 |
| | | | 424/401 |
| 2012/0288458 A1 | 11/2012 | Yamaguchi et al. | |
| 2013/0121939 A1 | 5/2013 | Fukuhara | |
| 2014/0010775 A1 | 1/2014 | Sonoyama et al. | |
| 2014/0205552 A1 | 7/2014 | Fukuhara | |
| 2016/0058677 A1 | 3/2016 | Kitajima et al. | |
| 2016/0113860 A1* | 4/2016 | Kikuchi | A61Q 19/00 |
| | | | 424/59 |

FOREIGN PATENT DOCUMENTS

| | | |
|---|---|---|
| JP | H1-180237 | 7/1989 |
| JP | A HEI 8217619 | 8/1996 |
| JP | H8-217619 | 8/1996 |
| JP | H08217618 | 8/1996 |
| JP | H108217618 A | 8/1996 |
| JP | H09255543 | 9/1997 |
| JP | H09255543 A | 9/1997 |
| JP | 9-301823 | 11/1997 |
| JP | 10-513188 | 12/1998 |
| JP | 2000-63233 | 2/2000 |
| JP | 2000063233 A | 2/2000 |
| JP | 2000-72646 | 3/2000 |
| JP | 2001187711 A | 7/2001 |
| JP | 2002-193741 | 7/2002 |
| JP | 2002/193741 A | 7/2002 |
| JP | 2004-83541 | 3/2004 |
| JP | 2004091374 A | 3/2004 |
| JP | 2005053846 A | 3/2005 |
| JP | 2007-217380 | 8/2007 |
| JP | 2007-332295 A | 12/2007 |
| JP | 2007332295 A | 12/2007 |
| JP | 2009-40738 | 2/2009 |
| JP | WO2011049248 | 3/2011 |
| JP | 2011-126832 | 6/2011 |
| JP | 2011111401 A | 6/2011 |
| JP | 2011126832 A | 6/2011 |
| JP | 2011-153079 | 8/2011 |
| JP | 2011-153079 A | 8/2011 |
| JP | 2011/225518 A | 11/2011 |
| JP | 2012-188. 394 | 10/2012 |
| JP | 2012-197241 A | 10/2012 |
| JP | 2012197241 A | 10/2012 |
| JP | 2012-219029 | 11/2012 |
| JP | 2014088369 A | 5/2014 |
| JP | 2014201541 A | 10/2014 |
| JP | 2014224075 A | 12/2014 |
| JP | 2015-189671 A | 11/2015 |
| WO | WO2009/119000 A | 10/2009 |
| WO | WO 2011/049248 | 4/2011 |
| WO | WO2011049248 A1 | 4/2011 |
| WO | WO-2012121309 A1 * | 9/2012 ............... A61Q 1/02 |
| WO | WO 2015/138491 A1 | 10/2013 |

OTHER PUBLICATIONS

Glenn Corp. ABIL®em 90, Emulsifier for the formulation of cosmetic W/O creams and lotions, Evonik Indusries, published Apr. 2008, p. 1-7.

Notice of Reasons for Revocation dated Nov. 14, 2018, 28 pages—English.

EP 17789264.3, Extended European Report dated Nov. 22, 2019, 8 pages - English.

PCT/JP2016/079962, International Search Report and Written Opinion, dated Dec. 20, 2016, 15 pages—English, 11 pages—Japanese.

Fragrance Journal May 1999, Rayleigh, Proc. Roy Soc. 84A; Kingerty W.O. Bowen, H.K. and Uhlman, 1 page—English, 5 pages—Japanese (pp. 79-83).

EP15854207.6, Search Report dated May 4, 2018, 7 pages—English.

JP 2018-514253 Office Action dated Apr. 3, 2021, 6 pages—Japanese, 7 pages—English.

* cited by examiner

WATER-IN-OIL TYPE EMULSIFIED COSMETIC

CROSS REFERENCE TO RELATED APPLICATIONS

This application relates to and claims priority as a § 371 national phase, from PCT/JP2017/014935 filed Apr. 12, 2017, the entire contents of which are incorporated herein by reference, which in turn claims priority from JP 2016-091449 filed Apr. 28, 2016.

FIGURE SELECTED FOR PUBLICATION

None

TECHNICAL FIELD

The present invention relates to a water-in-oil type emulsified cosmetic. More specifically, the present invention relates to a water-in-oil type emulsified cosmetic that has the unprecedented property, wherein upon coming into contact with perspiration, water even including such as pool water, seawater, rain and so forth, the vibrant color development and the color uniformity (homogeneity) are substantially improved over conditions immediately after application.

BACKGROUND ART

Emulsified cosmetics containing colorants are applied to various types of makeup cosmetics and hair-care cosmetics, such as emulsified foundations, BB (blemish balm) creams, body lotions and gray-hair concealers. In particular, water-in-oil type emulsified cosmetics have a continuous phase consisting of oil phase ingredients and leave an oil film, through which water cannot easily penetrate, on the skin surface, so that they have been considered to be a formula having relatively superior makeup durability. However, even in this formula, the outflow of colorants due to water from perspiration or the like is deemed as a significant problem, and research and development is continuously being performed for the purpose of preventing the occurrence of color loss, uneven coloring and staining under severe usage conditions.

On the other hand, the problem of protecting the skin and hair from damage due to ultraviolet rays is important in skin-care, body-care and hair-care, it has recently come to be considered important to provide protection from ultraviolet rays, not only under the severe ultraviolet ray conditions that occur during outdoor activities such as when swimming in a pool or in the sea during the summer or when skiing during the winter, but also in everyday life activities. For this reason, ultraviolet ray protection effects are sought and ideal even in normal makeup cosmetics, hair-care cosmetics and the like.

As with the colorants mentioned above, outflow by coming into contact with water is also considered to be a problem against ultraviolet ray absorbing agents and ultraviolet ray scattering agents, and various attempts have been made to improve the water resistance and film strength of cosmetics and the like in order to prevent decreasing ultraviolet ray protection effects as a result thereof (Patent Document 1 and Patent Document 2). However, it is difficult to completely prevent the outflow of ultraviolet ray absorbing agents, ultraviolet ray scattering agents and the like despite blending in high concentrations of resins or film agents in order to impart water resistance.

Thus, until now, there have been wide-ranging efforts to prevent the outflow of colorants, ultraviolet ray absorbing agents and the like, and it has been commonly thought that the highest color development, the best color uniformity and/or the strongest ultraviolet ray protection effects are provided immediately after application, and as a common sense, whereas such desirable effects lessen and worsen over time while being exposed to and contacting with perspiration, rain or the like, the conditions (effective results) obtained immediately after application has been never improved or even regained over time.

RELATED ART DOCUMENTS

Patent Documents

Patent Document 1: JP H1-180237 A
Patent Document 2: JP H8-217619 A

SUMMARY OF THE INVENTION

Problems to be Solved by the Invention

The present invention has the purpose of providing a water-in-oil type emulsified cosmetic having the unprecedented and innovative property wherein the color development and color uniformity are maintained, and even the effects conversely improve, by coming into contact with perspiration or water such as pool water, seawater and rain.

Means for Solving the Problems

As a result of performing diligent research towards solving the aforementioned problem, the present inventors found that, by blending an organically modified clay mineral and another oil-phase thickener so as to have a predetermined mass ratio relative to non-volatile liquid oils excluding silicone oils, and further combining a specific silicone-based surfactant therewith, it is possible to obtain an emulsified cosmetic in which, by coming into contact with water or perspiration, the film uniformity increases over the conditions at the time of application, and which thus has the aforementioned novel properties, thereby completing the present invention.

In other words, the present invention provides a water-in-oil type emulsified cosmetic comprising:
(A) an organically modified clay mineral;
(B) an oil phase thickener other than the (A) organically modified clay mineral;
(C) a non-volatile liquid oil other than a silicone oil;
(D) a silicone-based surfactant having an HLB of less than 8; and
(E) a colorant;
  wherein a weight ratio defined by [(A)+(B)]/(C) is at least 0.04 and less than 0.68.

Effects of the Invention

By being constituted as described above, the present invention has the property wherein, after coming into contact with perspiration or water such as pool water, seawater or rain, the color development and the color uniformity are significantly improved over the conditions immediately after application of the cosmetic to the skin or hair. In other words, the water-in-oil type emulsified cosmetic according to the present invention is an innovative cosmetic having properties that are the opposite of the conventional wisdom in that contact with water, which was considered to cause deterioration of the effects in conventional cosmetics, conversely improves the color development and the color uniformity.

Furthermore, the cosmetic of the present invention achieves excellent color development and ultraviolet ray protection effects even without formulating high concentrations of resins or film agents for imparting water resistance, so that such a cosmetic provides no filmy sensation, spreads well at the time of use (the time of application) and is easily removable with conventional detergents or soaps.

MODES FOR CARRYING OUT THE INVENTION

As mentioned above, the water-in-oil type emulsified cosmetic of the present invention comprises:
(A) an organically modified clay mineral; (B) an oil phase thickener other than the (A) organically modified clay mineral; (C) a non-volatile liquid oil other than a silicone oil; (D) a silicone-based surfactant having an HLB of less than 8; and (E) a colorant; wherein a weight ratio defined by [(A)+(B)]/(C) is at least 0.04 and less than 0.68. Herebelow, the ingredients constituting the emulsified cosmetic of the present invention will be explained in detail.

<(A) Organically Modified Clay Mineral>

As the (A) organically modified clay mineral (hereinafter sometimes referred to simply as "ingredient (A)"), it is possible to use a clay mineral modified by a quaternary ammonium salt type cationic surfactant, represented by the following general formula (1), which is a type of colloidal hydrated aluminum silicate having a three-layered structure.

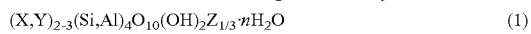

$$(X,Y)_{2-3}(Si,Al)_4O_{10}(OH)_2Z_{1/3} \cdot nH_2O \qquad (1)$$

where X is Al, Fe(III), Mn(III) or Cr(III); Y is Mg, Fe(II), Ni, Zn or Li; and Z is K, Na or Ca.

Specifically, the ingredient can be obtained by treating with a quaternary ammonium salt type cationic surfactant, a clay mineral which may be a natural or synthetic (in this case, an (OH) group in the formula is substituted with a fluorine) clay mineral in the montmorillonite group, such as montmorillonite, saponite or hectorite (commercial products include Veegum®, Kunipia, Laponite®, etc.), or a synthetic mica known under the name of sodium silicic mica or sodium or lithium taeniolite (commercial products include Dimonite, manufactured by Topy Industries, etc.).

The quaternary ammonium salt type cationic surfactant used in this case is represented by the following general formula (2):

[Chemical Formula 1]

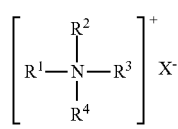

$$\left[ \begin{array}{c} R^2 \\ | \\ R^1-N-R^3 \\ | \\ R^4 \end{array} \right]^+ X^- \qquad (2)$$

where $R^1$ represents an alkyl group or a benzyl group having 10 to 22 carbon atoms, $R^2$ represents a methyl group or an alkyl group having 10 to 22 carbon atoms, $R^3$ and $R^4$ represent alkyl groups or hydroxyalkyl groups having 1 to 3 carbon atoms, and X represents a halogen atom or a methylsulfate residue.

Examples of the quaternary ammonium salt type cationic surfactant include dodecyltrimethylammonium chloride, myristyltrimethylammonium chloride, cetyltrimethylammonium chloride, stearyltrimethylammonium chloride, arachyltrimethylammonium chloride, behenyltrimethylammonium chloride, myristyldimethylethylammonium chloride, cetyldimethylethylammonium chloride, stearyldimethylethylammonium chloride, arachyldimethylethylammonium chloride, behenyldimethylethylammonium chloride, myristyldiethylmethylammonium chloride, cetyldiethylmethylammonium chloride, stearyldiethylmethylammonium chloride, arachyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, dibehenyldihydroxyethylammonium chloride, and corresponding bromides and the like, and further thereto, dipalmitylpropylethylammonium methylsulfate and the like. When carrying out the present invention, one or more of these compounds may be freely chosen.

Representative examples of ingredient (A) include dimethyldistearylammonium hectorite (disteardimonium hectorite), dimethylalkylammonium hectorite, benzyldimethylstearylammonium hectorite, distearyldimethylammonium-chloride-treated aluminum-magnesium silicate and the like. Of these, dimethyldistearylammonium hectorite is particularly preferred. As commercial products, Bentone® 27 (benzyldimethylstearylammonium-chloride-treated hectorite, manufactured by Elementis Japan) and Bentone® 38 (distearyldimethylammonium-chloride-treated hectorite, manufactured by Elementis Japan) are preferred.

In the present invention, it is possible to use one or a combination of two or more of the ingredients corresponding to (A).

The blended amount of ingredient (A) is 0.1 to 3% by mass, preferably 0.2 to 2% by mass, more preferably 0.4 to 1% by mass with respect to the overall amount of the water-in-oil type emulsified cosmetic. If the blended amount of ingredient (A) is less than 0.1% by mass, it is difficult to obtain sufficient stability, and if added in excess of 3% by mass, the viscosity becomes high and it is undesirable in terms of the properties when used, such as becoming heavy to spread over the skin.

<(B) Oil Phase Thickener>

The (B) oil phase thickener (hereinafter sometimes referred to simply as "ingredient (B)") is a substance, other than ingredient (A), that can adjust the viscosity of the oil phase. For example, dextrin fatty acid esters, sucrose fatty acid esters, and fatty acids or salts thereof that are solid at ambient temperature, hydrogenated vegetable oils and the like are preferable, and it is particularly preferable to blend two or more thickeners chosen from the above.

Dextrin fatty acid esters are esters of dextrin or reduced dextrin with a higher fatty acid, which may be used without any particular restrictions as long as they are generally used in cosmetics. As the dextrin or reduced dextrin, one in which the average degree of polymerization in the sugars is 3 to 100 is preferably used. Additionally, as the fatty acids constituting the dextrin fatty acid ester, a saturated fatty acid having 8 to 22 carbon atoms is preferable. Specific examples include dextrin palmitate, dextrin oleate, dextrin stearate, dextrin myristate, dextrin (palmitate/2-ethylhexanoate) and the like.

As the sucrose fatty acid ester, one in which the fatty acid is linear or branched, saturated or unsaturated, and has 12 to 22 carbon atoms is preferably used. Specific examples include sucrose caprylic acid esters, sucrose capric acid esters, sucrose lauric acid esters, sucrose myristic acid esters, sucrose palmitic acid esters, sucrose stearic acid esters, sucrose oleic acid esters, sucrose erucic acid esters and the like.

The solid fatty acid at ambient temperature may be used, and examples include myristic acid, palmitic acid, stearic acid, behenic acid and the like. Additionally, the fatty acid salt may be a calcium salt, a magnesium salt, an aluminum salt or the like thereof.

Examples of the hydrogenated vegetable oil include hydrogenated palm kernel oil, hydrogenated castor oil, hydrogenated peanut oil, hydrogenated rapeseed oil, hydrogenated palm oil, hydrogenated camellia oil, hydrogenated soy oil, hydrogenated olive oil, hydrogenated macadamia nut oil, hydrogenated sunflower oil, hydrogenated wheat germ oil, hydrogenated rice germ oil, hydrogenated rice bran oil, hydrogenated cottonseed oil, hydrogenated avocado oil and the like.

The blended amount of ingredient (B) is 0.1 to 15% by mass, preferably 0.2 to 10% by mass, more preferably 0.4 to 8% by mass with respect to the overall amount of the water-in-oil type emulsified cosmetic. If the blended amount of ingredient (B) is less than 0.1% by mass, it is difficult to obtain sufficient stability, and if the blended amount of ingredient (B) is more than 15% by mass, the viscosity becomes high, so that it is undesirable in terms of the properties when used due to such as becoming heavy to spread over the skin.

For reasons of stability over time and control of the viscosity, it is preferable to additionally formulate at least one of a second (A) organically modified clay mineral selected from a group of organically modified clay minerals and a second (B) oil phase thickener selected from a group of oil phase thickeners.

<(C) Non-Volatile Liquid Oil Other than Silicone Oil>

The cosmetic in the present invention is a water-in-oil type emulsified cosmetic, and must contain an oil constituting the external phase (continuous phase). The oils in the present invention include a non-volatile liquid oil and may further include a volatile oil.

In the present specification, a "non-volatile liquid oil" refers to a liquid oil that does not exhibit volatility at ambient temperature (25° C.) and ambient pressure (1 atm ($9.8 \times 10^4$ Pa)) (for example, oils having a boiling point of approximately 200° C. or higher at ambient pressure are included), that is fluid at ambient temperature and ambient pressure, and that is not solid, including silicone oils and non-volatile oils other than silicone oils (such as hydrocarbon oils, ester oils and the like).

The present invention essentially contains a non-volatile liquid oil other than a silicone oil (hereinafter referred to as "ingredient (C)". This ingredient (C) may include oil-based ultraviolet ray absorbing agents as mentioned hereinbelow. Therefore, there may be cases in which all of the (C) non-volatile liquid oils other than silicone oil consist of ultraviolet ray absorbing agents. By blending in an ultraviolet ray absorbing agent, one can expect not only color development and color uniformity when coming into contact with water, but also improved ultraviolet ray protection effects.

Non-volatile liquid oils that may be included in ingredient (C) but that are not ultraviolet ray absorbing agents include, for example, hydrocarbon oils, vegetable oils, ester oils, and high-molecular-weight polyoxyalkylene glycols.

Specific examples include liquid oils and fats such as linseed oil, camellia oil, macadamia nut oil, corn oil, olive oil, avocado oil, sasanqua oil, castor oil, safflower oil, apricot kernel oil, cinnamon oil, jojoba oil, grape oil, almond oil, rapeseed oil, sesame oil, sunflower oil, wheat germ oil, rice germ oil, rice bran oil, cottonseed oil, soy oil, peanut oil, tea seed oil, evening primrose oil, egg yolk oil, liver oil, triglycerin, glyceryl trioctanoate and glyceryl triisopalmitate; fatty acids that are liquid at ambient temperature, such as isostearic acid; ester oils including octanoic acid esters such as cetyl octanoate, iso-octanoic acid esters such as glyceryl tri-2-ethylhexanoate and pentaerythritol tetra-2-ethylhexanoate, lauric acid esters such as hexyl laurate, myristic acid esters such as isopropyl myristate and octyldodecyl myristate, palmitic acid esters such as octyl palmitate, stearic acid esters such as isocetyl stearate, isostearic acid esters such as isopropyl isostearate, isopalmitic acid esters such as octyl isopalmitate, oleic acid esters such as isodecyl oleate, adipic acid diesters such as diisopropyl adipate, sebacic acid diesters such as diethyl sebacate and diisopropyl sebacate, and diisotearyl malate; hydrocarbon oils such as liquid paraffin and squalane; and polyoxybutylene polyoxypropylene glycol.

The liquid and oil-based ultraviolet ray absorbing agent contained in ingredient (C) is not particularly limited, but specific examples include organic ultraviolet ray absorbing agents such as ethylhexyl methoxycinnamate, octocrylene, polysilicon-15, homosalate and ethylhexyl salicylate.

Solid ultraviolet ray absorbing agents such as diethylamino hydroxybenzoyl hexyl benzoate, bis-ethylhexyloxyphenol methoxyphenyl triazine, t-butyl methoxydibenzoyl methane, ethylhexyl triazone, oxybenzone-3, methylene bis-benzotriazolyl tetramethylbutylphenol and the like are not included in ingredient (C).

The blended amount of ingredient (C) is at least 3% by mass, preferably 5 to 50% by mass, and more preferably 7 to 30% by mass with respect to the overall amount of the water-in-oil type emulsified cosmetic. If the blended amount of ingredient (C) lies outside the above-mentioned range, in addition to the effects of the present invention not being able to be achieved, the emulsion stability and texture may be degraded.

The cosmetic of the present invention preferably contains, as an oil, a volatile oil other than ingredient (C). As the volatile oil, a volatile hydrocarbon oil and a volatile silicone oil may be blended, and in particular, it is preferable to blend a volatile silicone oil.

The volatile hydrocarbon oil is not particularly limited as long as it is a hydrocarbon oil that is volatile at ambient temperature (25° C.) and is conventionally used in cosmetics and the like. Specific examples include isododecane, isohexadecane, hydrogenated polyisobutene and the like.

The volatile silicone oils include silicone oils that are volatile at ambient temperature and that are conventionally used in cosmetics and the like. Examples include volatile linear silicone oils (volatile dimethicones) and volatile cyclic silicone oils (volatile cyclodimethicones). Examples of volatile dimethicones include low-viscosity dimethylpolysiloxanes such as decamethyltetrasiloxane or the like, and commercial products include KF-96L-1.5 cs and KF-96-2 cs (both manufactured by Shin-Etsu Chemical) or the like. An example of a volatile cyclomethicone is decamethylcyclopentasiloxane (D5) or the like.

The blended amount of the volatile oil is not particularly limited, but should normally be about 1-40% by mass relative to the overall amount of the water-in-oil type emulsified cosmetic.

<Weight Ratio [(A)+(B)]/(C)>

In the water-in-oil type emulsified cosmetic according to the present invention, the total amount of the ingredients (A) and (B) involved with the adjustment of the viscosity of the oil phase must have a predetermined weight ratio with respect to the total weight of ingredient (C).

In other words, the weight ratio [(A)+(B)]/(C) must essentially be at least 0.04 and less than 0.68, and further thereto, this ratio should preferably be at least 0.045 and less than 0.5. If the ratio is less than 0.04 or is 0.68 or higher, improvements in the color development and color uniformity upon coming into contact with water are not observed.

<(D) Silicone-Based Surfactant Having an HLB of Less than 8>

The (D) silicone-based surfactant (hereinafter sometimes referred to simply as "ingredient (D)") has a silicone backbone (polysiloxane structure) and is not particularly limited as long as it is a surfactant having an HLB of less than 8. For example, the use of a polyoxyalkylene-modified silicone, a polyoxyalkylene/alkyl-comodified silicone, a polyglycerin-modified silicone and/or a polyglycerin/alkyl-comodified silicone is preferred, and a polyoxyalkylene-modified silicone and a polyoxyalkylene/alkyl-modified silicone are particularly preferred.

The polyoxyalkylene-modified silicone used in the present invention has a linear or branched organopolysiloxane as the main backbone and has a polyoxyalkylene group on a side chain. For example, it may be a compound expressed by the following general formula (3).

[Chemical Formula 2]

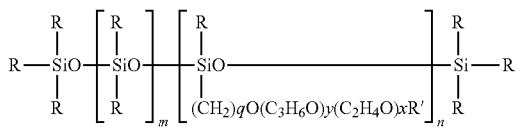

(3)

In general formula (3), R represents a phenyl group or an alkyl group having 1 to 3 carbon atoms (preferably a methyl group), R' represents hydrogen or an alkyl group having 1 to 12 carbon atoms (preferably hydrogen or a methyl group), q is 1 to 50 (preferably 3), m is 1 to 100, n and x are each 1 to 50, and y is 0 to 50. A preferable example of a polyoxyalkylene-modified silicone is KF-6017 (PEG-10 dimethicone, manufactured by Shin-Etsu Chemical).

Additionally, in the above-indicated formula (3), the organopolysiloxane main backbone may have another organopolysiloxane chain as a side chain. A suitable example of such a polyoxyalkylene-modified silicone is KF-6028 (PEG-9 polydimethylsiloxyethyl dimethicone, manufactured by Shin-Etsu Chemical).

The polyoxyalkylene/alkyl-modified silicone used in the present invention has a linear or branched organopolysiloxane as the main backbone and has a polyoxyalkylene group and an alkyl group having 4 or more carbon atoms on a side chain. For example, it may be a compound expressed by the following general formula (4).

[Chemical Formula 3]

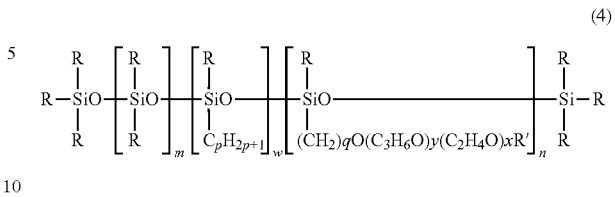

(4)

In general formula (4), R represents a phenyl group or an alkyl group having 1 to 3 carbon atoms (preferably a methyl group), R' represents hydrogen or an alkyl group having 1 to 12 carbon atoms (preferably hydrogen), p is 6 to 30 (preferably 10 to 18, more preferably 12 to 16), q is 1 to 50 (preferably 3), m is 1 to 100, n, w and x are each 1 to 50, and y is 0 to 50. A suitable example of a polyoxyalkylene/alkyl-comodified silicone is ABIL® EM90 (cetyl PEG/PPG-10/1 dimethicone, manufactured by Evonik Goldschmidt).

Additionally, in the above-indicated general formula (4), the organopolysiloxane main backbone may have another organopolysiloxane chain as a side chain. A preferable example of such a polyoxyalkylene/alkyl-modified silicone is KF-6038 (lauryl PEG-9 polydimethylsiloxyethyl dimethicone, manufactured by Shin-Etsu Chemical).

The polyglycerin-modified silicone may, for example, be the linear polyglycerin-modified silicone (i.e., polyglycerin with silicones at both ends) expressed by the following general formula (5):

[Chemical Formula 4]

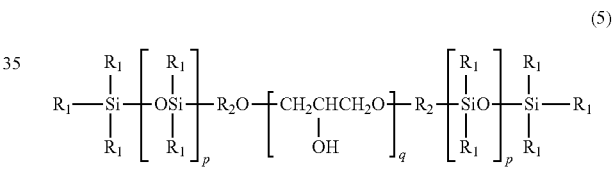

(5)

where $R_1$ represents a linear or branched alkyl group having 1 to 12 carbon atoms, or a phenyl group, $R_2$ represents an alkylene group having 2 to 11 carbon atoms, p is 10 to 120, and q is 1 to 11. Specific examples include bis-butyldimethicone polyglycerol-3 and the like.

The polyglycerin/alkyl-comodified silicone has a linear or branched organopolysiloxane as the main backbone and has a polyglycerin group and an alkyl group having 4 or more carbon atoms on a side chain. An example thereof is KF-6105 (lauryl polyglyceryl-3 polydimethylsiloxyethyl dimethicone, manufactured by Shin-Etsu Chemical).

The blended amount of ingredient (D) is 0.1 to 8% by mass, preferably 0.2 to 7% by mass, more preferably 0.4 to 5% by mass with respect to the overall amount of the water-in-oil type emulsified cosmetic. If the blended amount of ingredient (D) is less than 0.1% by mass, it is difficult to obtain sufficient stability, and if the blended amount of ingredient (D) is added in excess of 8% by mass, the viscosity becomes high and it is undesirable in terms of the properties when used due to such as becoming heavy to spread over the skin.

<(E) Colorant>

As the (E) colorant (hereinafter referred to simply as "ingredient (E)") blended in the water-in-oil type emulsified cosmetic according to the present invention, it is possible to use a type that is normally blended into makeup cosmetics such as pigments and pearl pigments.

Specifically, it is possible to choose one or more inorganic white pigments (titanium dioxide and zinc oxide), inorganic red pigments (red iron oxide and iron titanate), inorganic brown pigments (γ-ferric oxide), inorganic yellow pigments (yellow iron oxide and loess), inorganic black pigments (black iron oxide, carbon and lower titanium oxides), inorganic violet pigments (mango violet and cobalt violet), inorganic green pigments (chromium oxide, chromium hydroxide and cobalt titanate), inorganic blue pigments (ultramarine blue and Prussian blue), pearl pigments (titanium-oxide-coated mica, titanium-oxide-coated bismuth oxychloride, titanium-oxide-coated talc, colored titanium-oxide-coated mica, bismuth oxychloride and argentine), metal powder pigments (aluminum powder and copper powder), organic pigments (Red No. 202, Red No. 205, Red No. 220, Red No. 228, Red No. 405, Orange No. 203, Orange No. 204, Yellow No. 205, Yellow No. 401 and Blue No. 404), zirconium, barium and aluminum lake organic pigments (Red No. 3, Red No. 104, Red No. 227, Red No. 401, Orange No. 205, Yellow No. 4, Yellow No. 202, Green No. 3 and Blue No. 1), natural pigments (chlorophyll, carotenoids (β-carotene), carthamin, cochineal, chalcone, curcumin, betanin, flavonols, flavones, anthocyanidins, anthraquinones and naphthoquinones) and functional pigments (boron nitride, photochromic pigments, synthetic fluorophlogopite, iron-containing synthetic fluorophlogopite and fine-particle composite powders (hybrid fine powders)). However, the present invention is not to be construed as being limited thereto.

When the colorants are particulate, the weight-average particle size should preferably be 300 μm or less, more preferably 200 μm or less and even more preferably 100 μm or less. By blending a particulate colorant having a weight-average particle size of 300 μm or less, there is a tendency for the color development and color uniformity when coming into contact with water to improve significantly.

It is possible to use a powdered colorant that is not surface-treated, or to use one that is surface-treated by means of organosilane compounds, silicone compounds, fluorine compounds, silane couplers, fluororesins, fatty acids, fatty acid soaps, lauroyl lysine or the like.

Even among colorants, it is preferable to blend pearl pigments due to the significant increase in the amount of diffusively reflected light after exposure to water. The higher the amount of diffusively reflected light, the more the glossiness of the skin tends to increase.

The blended amount of ingredient (E) should be at least 0.3% by mass, more preferably 0.5 to 20% by mass with respect to the overall amount of the water-in-oil type emulsified cosmetic. If the blended amount of ingredient (E) is less than 0.3% by mass, it is difficult to obtain sufficient color development, and it is not favorable to blend in more than 20% by mass, because this causes the stability to become worse.

Aside from the above-mentioned essential ingredients, it is possible to blend, as appropriate and as needed, into the water-in-oil type emulsified cosmetic of the present invention, ingredients that are normally used in cosmetics, for example, whitening agents, humectants, anti-oxidants, oil-based active agents, surfactants, water-phase thickeners, alcohols, spherical powder ingredients, aqueous active agents and the like. Additionally, the water-in-oil type emulsified cosmetic may be produced by means of conventional methods.

Among the above, it is preferable to blend in approximately 1 to 30% by mass of spherical resin powders, since this further improves feeling in use and allows a good, non-sticky texture to be obtained. The spherical resin powder used in the present invention may be freely used without any particular limitations, as long as it is of a type that is blended into cosmetic products or the like in general. Examples include (meth)acrylic acid ester resin powders, polyamide resin powders (nylon powders), polyethylene powders, polystyrene powders, styrene/(meth)acrylic acid copolymer resin powders, benzoguanamine resin powders, polytetrafluoroethylene powders, cellulose powders, trimethyl silsesquioxane powders and the like, as well as organopolysiloxane elastomer spherical powders or composite spherical powders having the same as base powders. Although the particle sizes or the like of the blended spherical resin powders are not particularly limited, one in which the particle size is, for example, approximately 1 to 50 μm may be favorably used. Additionally, these resin powders may be subjected to hydrophobization treatments. An example of a commercially available spherical organic resin powder is Ganzpearl (manufactured by Aica Kogyo), and examples of commercially available spherical silicone resin powders include Trefil E-505C, Trefil E-506C, Trefil E-506S, Trefil HP40T (all manufactured by Toray Dow Corning Silicone), Tospearl 145A (manufactured by Toshiba Silicone), and silicone powders KSP-100 and KSP-300 (manufactured by Shin-Etsu Chemical) and the like.

The water-in-oil type emulsified cosmetic of the present invention can be used as a foundation, a makeup base, a makeup cosmetic, a hair cosmetic or the like, optionally having a sunscreen effect.

EXAMPLES

While the present invention will be explained in further detail by providing specific examples below, the present invention is not to be construed as being limited to the following examples. Additionally, the blended amounts in the following examples and the like are expressed in % by mass where not stated otherwise.

In Production Examples 1 to 38, ultraviolet ray protectants were blended instead of the colorants (ingredient (E)) in the present invention in order to investigate the change in the effects of the blended ingredients due to coming into contact with water, by considering the ultraviolet ray protection effects. On the other hand, in Production Examples 39 to 59 containing ingredient (E), the change in the diffusively reflected light amount or the color development based on the color difference before and after exposure to water were directly investigated.

Production Examples 1 to 12

The water-in-oil type emulsified cosmetics having the compositions indicated in Table 1 below were prepared by heating and dissolving the oil-based components, dispersing the powders therein, adding the separately dissolved water phase, and emulsifying by means of agitation.

Measurement of Ultraviolet Ray Protection Effect

Cosmetics (samples) of each example were dripped, in the amount of 2 mg/cm$^2$, onto measurement plates (S plates) (5×5 cm V-groove PMMA plate, SPFMASTER-PA01), spread by finger for 60 seconds, dried for 15 minutes, then the absorbances thereof were measured using a Hitachi U-3500 self-recording spectrophotometer. An uncoated S plate was used as the control, and the absorbance (Abs) was computed by using the following formula.

$$Abs = -\log(T/T_0)$$

T: sample transmittance, To: transmittance of uncoated S plate

The measured plates were fully immersed in water having a hardness of 50 to 500, and agitated (300 rpm using a 3-1 motor) in the water for 30 minutes. Thereafter, the plates were dried for about 15 to 30 minutes until the water droplets on the surfaces disappeared, the absorbances were measured again, and the Abs change percentage (see formula below) was computed, as the ultraviolet ray protection performance improvement effect, from the Abs integral values before and after exposure to water.

Ultraviolet Ray Protection Performance Improvement Effect:

$$\text{Abs change percentage}(\%) = (\text{Abs integral value after water})/(\text{Abs integral value before water}) \times 100$$

in the tables, when a silicone-based non-volatile liquid oil was added instead of component (C), a stable emulsion was not obtained.

Production Examples 13 and 14

A water-in-oil type emulsified cosmetic having the composition indicated in Table 2 below was prepared, and the percentages by which the absorbance changed before/after exposure to water were determined in the same manner as above.

TABLE 1

| | Prod. Ex. 1 | Prod. Ex. 2 | Prod. Ex. 3 | Prod. Ex. 4 | Prod. Ex. 5 | Prod. Ex. 6 | Prod. Ex. 7 | Prod. Ex. 8 | Prod. Ex. 9 | Prod. Ex. 10 | Prod. Ex. 11 | Prod. Ex. 12 |
|---|---|---|---|---|---|---|---|---|---|---|---|---|
| Light isoparaffin | bal | bal | bal | bal | bal | bal | bal | bal | bal | bal | bal | bal |
| PEG-9 Polydimethylsiloxyethyl dimethicone | 1.5 | 1.5 | 1.5 | 1.5 | 1.5 | 1.5 | 1.5 | 1.5 | 1.5 | 1.5 | 1.5 | 1.5 |
| Decamethyltetrasiloxane | 10 | 10 | 10 | 10 | 10 | 10 | 10 | 10 | 10 | 10 | 10 | 10 |
| Methyl polysiloxane (6 cs) | 4 | 4 | 4 | 4 | 4 | 4 | 4 | 4 | 4 | 4 | 4 | 4 |
| Dimethyldistearylammonium hectorite | — | 0.5 | 0.3 | 0.5 | 0.5 | 0.5 | 0.5 | 0.5 | 0.5 | 0.5 | 0.5 | 0.5 |
| Dextrin palmitate | — | — | 1 | 0.5 | 1 | 2 | 3 | 1 | 1 | 5 | 7.5 | 10 |
| Trimethyl siloxysilicate | 2 | 2 | 2 | 2 | 2 | 2 | 2 | 2 | 2 | 2 | 2 | 2 |
| Polyoxybutylene polyoxypropylene glycol | 2.5 | 2.5 | 2.5 | 2.5 | 2.5 | 2.5 | 2.5 | 2.5 | 2.5 | 2.5 | 2.5 | 2.5 |
| Isopropyl myristate | 3 | 3 | 3 | 3 | 3 | 3 | 3 | 3 | 30 | 3 | 3 | 3 |
| Octocrylene | 3 | 3 | 3 | 3 | 3 | 3 | 3 | 3 | 3 | 3 | 3 | 3 |
| Dimethicodiethyl benzalmalonate | 3 | 3 | 3 | 3 | 3 | 3 | 3 | 3 | 3 | 3 | 3 | 3 |
| 2-Ethylhexyl paramethoxycinnamate | 8 | 7 | 7 | 7 | 7 | 7 | 7 | 8 | 8 | 8 | 8 | 8 |
| 2,4-Bis-[{4-(2-ethylhexyloxy)-2-hydroxy}-phenyl]-6-(4-methoxyphenyl)-1,3,5-triazine | 1 | 1 | 1 | 1 | 1 | 1 | 1 | 1 | 1 | 1 | 1 | 1 |
| Diethylamino hydroxybenzoyl hexyl benzoate | 1 | 1 | 1 | 1 | 1 | 1 | 1 | 1 | 1 | 1 | 1 | 1 |
| Dimethicone-coated fine-particle zinc oxide | 10 | 10 | 10 | 10 | 10 | 10 | 10 | 10 | 10 | 10 | 10 | 10 |
| Methyl siloxane network polymer | 5 | 5 | 5 | 5 | 5 | 5 | 5 | 5 | 5 | — | — | — |
| Talc | 5 | 5 | 5 | 5 | 5 | 5 | 5 | 5 | 5 | 10 | 10 | 10 |
| Purified water | 10 | 10 | 10 | 10 | 10 | 10 | 10 | 10 | 10 | 10 | 10 | 10 |
| Trisodium edetate | q.s. | q.s. | q.s. | q.s. | q.s. | q.s. | q.s. | q.s. | q.s. | q.s. | q.s. | q.s. |
| Glycerin | 1 | 1 | 1 | 1 | 1 | 1 | 1 | 1 | 1 | 1 | 1 | 1 |
| Xylitol | 1 | 1 | 1 | 1 | 1 | 1 | 1 | 1 | 1 | 1 | 1 | 1 |
| Ethanol | 10 | 10 | 10 | 10 | 10 | 10 | 10 | 10 | 10 | 10 | 10 | 10 |
| Total | 100 | 100 | 100 | 100 | 100 | 100 | 100 | 100 | 100 | 100 | 100 | 100 |
| [(A) + (B)]/(C) weight ratio | 0.000 | 0.027 | 0.070 | 0.054 | 0.081 | 0.135 | 0.189 | 0.077 | 0.032 | 0.282 | 0.410 | 0.538 |
| Abs integral value before immersion | 174.8 | 170.2 | 160.1 | 180.4 | 155.5 | 153.4 | 148.9 | 173.1 | 197.1 | 146.1 | 123.4 | 132.7 |
| Abs integral value after immersion | 172.7 | 166.5 | 204.7 | 187.8 | 173.3 | 173.4 | 185.9 | 202.3 | 171.7 | 171.3 | 141.2 | 148.7 |
| Abs change (%) before/after immersion | 98.8 | 97.8 | 127.9 | 104.1 | 111.5 | 113.0 | 124.8 | 116.9 | 87.1 | 117.3 | 114.4 | 112.1 |

As shown in Table 1, when the weight ratio [(A)+(B)]/(C) was less than 0.04 (Production Examples (Prod. Ex.) 1, 2 and 9), the ultraviolet ray protection effects decreased after exposure to water. In contrast therewith, when the weight ratio [(A)+(B)]/(C) was within the range from at least 0.04 to less than 0.68 (Production Examples 3 to 8 and 10 to 12), the ultraviolet ray protection effects after exposure to water increased by a maximum of approximately 28% (Production Example 3) compared to the effects before exposure to water. This increase in the absorbance shows that the coated film was not lost due to perspiration or water, and the uniformity of the coated film increased. Though not shown

TABLE 2

| | Prod. Ex. 13 | Prod. Ex. 14 |
|---|---|---|
| Cyclomethicone | 40 | 37 |
| Glyceryl tri(2-ethylhexanoate) | 3 | 6 |
| 2-Ethylhexyl paramethoxycinnamate | 5 | 5 |
| Trimethyl siloxysilicate | 4 | 4 |
| PEG-10 dimethicone | 2 | 2 |
| Dimethyldistearylammonium hectorite | 0.5 | 0.5 |
| Dextrin palmitate | 5 | 5 |
| Dimethicone-coated fine-particle zinc oxide | 20 | 20 |
| Dimethicone-coated fine-particle titanium oxide | 5 | 5 |
| 1,3-Butylene glycol | 5 | 5 |

TABLE 2-continued

|  | Prod. Ex. 13 | Prod. Ex. 14 |
|---|---|---|
| Phenoxyethanol | 0.5 | 0.5 |
| Purified water | 10 | 10 |
| [(A) + (B)]/(C) weight ratio | 0.688 | 0.500 |
| Abs integral value before immersion | 159.3 | 154.7 |
| Abs integral value after immersion | 157.8 | 157.1 |
| Abs change (%) before/after immersion | 99.0 | 101.5 |

As shown in Table 2, in Production Example 13 in which the weight ratio [(A)+(B)]/(C) was at least 0.68 due to a difference in the blended amount of the non-volatile liquid oil, the ultraviolet ray protection effects decreased after exposure to water (immersion). In contrast therewith, in Production Example 14, wherein the ratio is within the range of the present invention, the ultraviolet ray protection effects after exposure to water improved over the effects before exposure to water.

From the results in Tables 1 and 2, it can be seen that the effects of the blended components (ultraviolet ray protectant) are improved by controlling the weight ratio [(A)+(B)]/(C) to be within the range defined in the present invention. This increase in the absorbance shows that the coated film was not lost due to perspiration or water, and the uniformity of the coated film increased.

Production Examples 15 to 23

Water-in-oil type emulsified cosmetics having the compositions shown in the following Tables 3 and 4 were prepared, and the percentages by which the absorbances changed before/after exposure to water were determined in the same manner as above.

TABLE 3

|  | Prod. Ex. 15 | Prod. Ex. 16 | Prod. Ex. 17 | Prod. Ex. 18 | Prod. Ex. 19 |
|---|---|---|---|---|---|
| Light isoparaffin | bal | bal | bal | bal | bal |
| PEG-9 polydimethylsiloxyethyl dimethicone | 1.5 | 1.5 | 1.5 | 1.5 | 1.5 |
| Decamethyltetrasiloxane | 10 | 10 | 10 | 10 | 10 |
| Methyl polysiloxane (6 cs) | 4 | 4 | 4 | 4 | 4 |
| Dimethyldistearylammonium hectorite | 0.5 | 0.5 | 0.5 | 0.5 | 0.5 |
| Sucrose fatty acid ester | — | 3 | — | — | — |
| Dextrin (palmitate/ethylhexanoate) | — | — | 3 | — | — |
| Magnesium stearate | — | — | — | 3 | — |
| Calcium stearate | — | — | — | — | 0.5 |
| Trimethyl siloxysilicate | 2 | 2 | 2 | 2 | 2 |
| Polyoxybutylene polyoxypropylene glycol | 2.5 | 2.5 | 2.5 | 2.5 | 2.5 |
| Isopropyl myristate | 3 | 3 | 3 | 3 | 3 |
| Octocrylene | 3 | 3 | 3 | 3 | 3 |
| Dimethicodiethyl benzalmalonate | 3 | 3 | 3 | 3 | 3 |
| 2-Ethylhexyl paramethoxycinnamate | 7 | 7 | 7 | 7 | 7 |
| 2,4-Bis-[{4-(2-ethylhexyloxy-2-hydroxy}-phenyl]-6-(4-methoxyphenyl)-1,3,5-triazine | 1 | 1 | 1 | 1 | 1 |
| Diethylamino hydroxybenzoyl hexyl benzoate | 1 | 1 | 1 | 1 | 1 |
| Dimethicone-coated fine-particle zinc oxide | 10 | 10 | 10 | 10 | 10 |
| Methyl siloxane network polymer | 5 | 5 | 5 | 5 | — |
| Talc | 5 | 5 | 5 | 5 | 10 |
| Purified water | 10 | 10 | 10 | 10 | 10 |
| Trisodium edetate | q.s. | q.s. | q.s. | q.s. | q.s. |
| Glycerin | 1 | 1 | 1 | 1 | 1 |
| Xylitol | 1 | 1 | 1 | 1 | 1 |
| Ethanol | 10 | 10 | 10 | 10 | 10 |
| Total | 100 | 100 | 100 | 100 | 100 |
| [(A) + (B)]/(C) weight ratio | 0.027 | 0.189 | 0.189 | 0.189 | 0.054 |
| Abs integral value before immersion | 170.2 | 188.9 | 162.5 | 185.7 | 163.8 |
| Abs integral value after immersion | 166.5 | 251.9 | 195.8 | 215.4 | 212.5 |
| Abs change (%) before/after immersion | 97.8 | 133.3 | 120.4 | 116.0 | 129.8 |

TABLE 4

|  | Prod. Ex. 20 | Prod. Ex. 21 | Prod. Ex. 22 | Prod. Ex. 23 |
|---|---|---|---|---|
| Light isoparaffin | bal | bal | bal | bal |
| PEG-9 Polydimethylsiloxyethyl dimethicone | 1.5 | 1.5 | 1.5 | 1.5 |
| Decamethyltetrasiloxane | 10 | 10 | 10 | 10 |
| Methyl polysiloxane (6 cs) | 4 | 4 | 4 | 4 |
| Dimethyldistearylammonium hectorite | 0.5 | 0.5 | 0.5 | 0.5 |
| Stearic acid | 1 | 3 | — | — |
| Behenic acid | — | — | 5 | — |
| Myristic acid | — | — | — | 5 |
| Trimethyl siloxysilicate | 2 | 2 | 2 | 2 |
| Polyoxybutylene polyoxypropylene glycol | 2.5 | 2.5 | 2.5 | 2.5 |
| Isopropyl myristate | 3 | 3 | 3 | 3 |

TABLE 4-continued

|  | Prod. Ex. 20 | Prod. Ex. 21 | Prod. Ex. 22 | Prod. Ex. 23 |
|---|---|---|---|---|
| Octocrylene | 3 | 3 | 3 | 3 |
| Dimethicodiethyl benzalmalonate | 3 | 3 | 3 | 3 |
| 2-Ethylhexyl paramethoxycinnamate | 7 | 7 | 7 | 7 |
| 2,4-Bis-[{4-(2-ethylhexyloxy)-2-hydroxy}-phenyl]-6-(4-methoxyphenyl)-1,3,5-triazine | 1 | 1 | 1 | 1 |
| Diethylamino hydroxybenzoyl hexyl benzoate | 1 | 1 | 1 | 1 |
| Dimethicone-coated fine-particle zinc oxide | 9 | 9 | 9 | 9 |
| Dimethicone-coated fine-particle titanium oxide | 1 | 1 | 1 | 1 |
| Methyl siloxane network polymer | 5 | 5 | 5 | 5 |
| Talc | 5 | 5 | 5 | 5 |
| Purified water | 10 | 10 | 10 | 10 |
| Trisodium edetate | q.s. | q.s. | q.s. | q.s. |
| Glycerin | 1 | 1 | 1 | 1 |
| Xylitol | 1 | 1 | 1 | 1 |
| Ethanol | 10 | 10 | 10 | 10 |
| Total | 100 | 100 | 100 | 100 |
| [(A) + (B)]/(C) weight ratio | 0.081 | 0.189 | 0.297 | 0.297 |
| Abs integral value before immersion | 155.6 | 148.6 | 135.9 | 147.2 |
| Abs integral value after immersion | 166.3 | 160.6 | 146.8 | 157.7 |
| Abs change (%) before/after immersion | 106.8 | 108.0 | 108.0 | 107.1 |

As shown in Tables 3 and 4, ultraviolet ray protection effects higher than those before exposure to water were obtained after exposure to water, even when the types of oil-phase thickeners (component (B)) were changed (Production Examples 16 to 23). However, when component (B) was not added, the ultraviolet ray protection effects after exposure to water decreased (Production Example 15). This decrease in absorbance shows that the coated film was lost due to perspiration and water, and that the uniformity of the coated film was reduced.

Production Examples 24 to 34

Water-in-oil type emulsified cosmetics having the compositions shown in the following Tables 5 and 6 were prepared, and the percentages by which the absorbances changed before/after exposure to water were determined in the same manner as above.

TABLE 5

|  | Prod. Ex. 24 | Prod. Ex. 25 | Prod. Ex. 26 | Prod. Ex. 27 | Prod. Ex. 28 |
|---|---|---|---|---|---|
| Light isoparaffin | bal | bal | bal | bal | bal |
| PEG-9 polydimethylsiloxyethyl dimethicone | 1.5 | — | — | — | — |
| Lauryl PEG-9 polydimethylsiloxyethyl dimethicone | — | 1.5 | — | — | — |
| PEG-10 dimethicone | — | — | 1.5 | — | — |
| Cetyl PEG/PPG-10/1-dimethicone | — | — | — | 1.5 | — |
| Bis-butyl dimethicone polyglyceryl-3 | — | — | — | — | 1.5 |
| Diglyceryl diisostearate | — | — | — | — | — |
| PEG-10 methyl ether dimethicone | — | — | — | — | — |
| PEG-12 dimethicone | — | — | — | — | — |
| PEG-8 diisostearate | — | — | — | — | — |
| Sorbitan sesquiisostearate | — | — | — | — | — |
| Sorbitan tristearate | — | — | — | — | — |
| Decamethyltetrasiloxane | 10 | 10 | 10 | 10 | 10 |
| Methyl polysiloxane (6 cs) | 4 | 4 | 4 | 4 | 4 |
| Dimethyldistearylammonium hectorite | 0.5 | 0.5 | 0.5 | 0.5 | 0.5 |
| Dextrin palmitate | 1 | 1 | 1 | 1 | 1 |
| Trimethyl siloxysilicate | 2 | 2 | 2 | 2 | 2 |
| Polyoxybutylene polyoxypropylene glycol | 2.5 | 2.5 | 2.5 | 2.5 | 2.5 |
| Isopropyl myristate | 3 | 3 | 3 | 3 | 3 |
| Octocrylene | 3 | 3 | 3 | 3 | 3 |
| Dimethicodiethyl benzalmalonate | 3 | 3 | 3 | 3 | 3 |
| 2-Ethylhexyl paramethoxycinnamate | 8 | 8 | 8 | 8 | 8 |
| 2,4-bis-[{4-(2-ethylhexyloxy)-2-hydroxy}-phenyl]-6-(4-methoxyphenyl)-1,3,5-triazine | 1 | 1 | 1 | 1 | 1 |
| Diethylamino hydroxybenzoyl hexyl benzoate | 1 | 1 | 1 | 1 | 1 |
| Dimethicone-coated fine-particle zinc oxide | 9 | 9 | 9 | 9 | 9 |
| Methyl siloxane network polymer | 5 | 5 | 5 | 5 | — |
| Talc | 5 | 5 | 5 | 5 | 10 |
| Purified water | 10 | 10 | 10 | 10 | 10 |

TABLE 5-continued

|  | Prod. Ex. 24 | Prod. Ex. 25 | Prod. Ex. 26 | Prod. Ex. 27 | Prod. Ex. 28 |
| --- | --- | --- | --- | --- | --- |
| Trisodium edetate | q.s. | q.s. | q.s. | q.s. | q.s. |
| Glycerin | 1 | 1 | 1 | 1 | 1 |
| Xylitol | 1 | 1 | 1 | 1 | 1 |
| Ethanol | 10 | 10 | 10 | 10 | 10 |
| Total | 100 | 100 | 100 | 100 | 100 |
| [(A) + (B)]/(C) weight ratio | 0.077 | 0.077 | 0.077 | 0.077 | 0.077 |
| HLB of (D) surfactant | 4.0 | 3.0 | 2 | 5.0 | 0.5 |
| Abs integral value before immersion | 163.0 | 166.7 | 158.0 | 153.1 | 153.3 |
| Abs integral value after immersion | 188.7 | 181.9 | 186.1 | 168.5 | 185.1 |
| Abs change (%) before/after immersion | 115.8 | 109.1 | 117.8 | 110.0 | 120.7 |

TABLE 6

|  | Prod. Ex. 29 | Prod. Ex. 30 | Prod. Ex. 31 | Prod. Ex. 32 | Prod. Ex. 33 | Prod. Ex. 34 |
| --- | --- | --- | --- | --- | --- | --- |
| Light isoparaffin | bal | bal | bal | bal | bal | bal |
| PEG-9 polydimethylsiloxyethyl dimethicone | — | — | — | — | — | — |
| Lauryl PEG-9 polydimethylsiloxyethyl dimethicone | — | — | — | — | — | — |
| PEG-10 dimethicone | — | — | — | — | — | — |
| Cetyl PEG/PPG-10/1-dimethicone | — | — | — | — | — | — |
| Bis-butyl dimethicone polyglyceryl-3 | — | — | — | — | — | — |
| Diglyceryl diisostearate | 1.5 | — | — | — | — | — |
| PEG-10 methyl ether dimethicone | — | 1.5 | — | — | — | — |
| PEG-12 dimethicone | — | — | 1.5 | — | — | — |
| PEG-8 diisostearate | — | — | — | 1.5 | — | — |
| Sorbitan sesquiisostearate | — | — | — | — | 1.5 | — |
| Sorbitan tristearate | — | — | — | — | — | 1.5 |
| Decamethyltetrasiloxane | 10 | 10 | 10 | 10 | 10 | 10 |
| Methyl polysiloxane (6 cs) | 4 | 4 | 4 | 4 | 4 | 4 |
| Dimethyldistearylammonium hectorite | 0.5 | 0.5 | 0.5 | 0.5 | 0.5 | 0.5 |
| Dextrin palmitate | 1 | 1 | 1 | 1 | 1 | 1 |
| Trimethyl siloxysilicate | 2 | 2 | 2 | 2 | 2 | 2 |
| Polyoxybutylene polyoxypropylene glycol | 2.5 | 2.5 | 2.5 | 2.5 | 2.5 | 2.5 |
| Isopropyl myristate | 3 | 3 | 3 | 3 | 3 | 3 |
| Octocrylene | 3 | 3 | 3 | 3 | 3 | 3 |
| Dimethicodiethyl benzalmalonate | 3 | 3 | 3 | 3 | 3 | 3 |
| 2-Ethylhexyl parametoxycinnamate | 8 | 8 | 8 | 8 | 8 | 8 |
| 2,4-bis-[{4-(2-ethylhexyloxy)-2-hydroxy}-phenyl]-6-(4-methoxyphenyl)-1,3,5-triazine | 1 | 1 | 1 | 1 | 1 | 1 |
| Diethylamino hydroxybenzoyl hexyl benzoate | 1 | 1 | 1 | 1 | 1 | 1 |
| Dimethicone-coated fine-particle zinc oxide | 9 | 9 | 9 | 9 | 9 | 9 |
| Methyl siloxane network polymer | — | — | — | — | — | — |
| Talc | 10 | 10 | 10 | 10 | 10 | 10 |
| Purified water | 10 | 10 | 10 | 10 | 10 | 10 |
| Trisodium edetate | q.s. | q.s. | q.s. | q.s. | q.s. | q.s. |
| Glycerin | 1 | 1 | 1 | 1 | 1 | 1 |
| Xylitol | 1 | 1 | 1 | 1 | 1 | 1 |
| Ethanol | 10 | 10 | 10 | 10 | 10 | 10 |
| Total | 100 | 100 | 100 | 100 | 100 | 100 |
| [(A) + (B)]/(C) weight ratio | 0.077 | 0.077 | 0.077 | 0.077 | 0.077 | 0.077 |
| HLB of (D) surfactant | 2.0 | 14 | 8 | 5 | 4.5 | 2.1 |
| Abs integral value before immersion | 164.8 | 170.9 | 175.3 | 147.9 | 157.8 | 167.9 |
| Abs integral value after immersion | 159.8 | 139.8 | 138.7 | 92.0 | 103.9 | 143.8 |
| Abs change (%) before/after immersion | 97.0 | 81.8 | 79.1 | 62.3 | 65.8 | 85.7 |

As shown in Tables 5 and 6, the ultraviolet ray protection effects decreased after exposure to water when surfactants other than silicone-based surfactants were used (Production Examples 29 and 32 to 34), and when a silicone-based surfactant having an HLB of 8 or higher was used (Production Examples 30 and 31). In contrast therewith, when a silicone-based surfactant having an HLB of less than 8 was used, the ultraviolet ray protection effects after exposure to water improved compared to the effects before exposure to water. This increase in absorbance shows that the coated film was not lost due to perspiration and water, and that the uniformity of the coated film was improved.

Production Examples 35-38

Water-in-oil type emulsified cosmetics having the compositions shown in the following Table 7 were prepared, and the percentages by which the absorbances changed before/after exposure to water were determined in the same manner as above.

Production Examples 39 to 50

Makeup cosmetics having the compositions shown in the following Tables 8 and 9 were prepared by heating and melting the oil-based component and dispersing powder components therein, then adding a separately dissolved water phase, and stirring to emulsify.

BioSkin® #420 (0.5 g pigment) was coated with 2 mg/cm$^2$ of the samples and the diffusively reflected light amount (integral value) before exposure to water was measured by using a SAMBA Hair System (Bossa Nova Technologies). Next, after immersion for 20 minutes in tap water, the samples were dried for approximately 15 to 30 minutes until the water droplets on the surface disappeared, and the diffusively reflected light amount (integral value) after expo-

TABLE 7

|  | Prod. Ex. 35 | Prod. Ex. 36 | Prod. Ex. 37 | Prod. Ex. 38 |
|---|---|---|---|---|
| Light isoparaffin | bal | bal | bal | bal |
| Polyoxyethylene-methyl polysiloxane copolymer | 1.5 | 1.5 | 1.5 | 1.5 |
| Decamethyltetrasiloxane | 10 | 10 | 10 | 10 |
| Methyl polysiloxane (6 cs) | 4 | 4 | 4 | 4 |
| Dimethyldistearylammonium hectorite | 0.5 | 0.5 | 0.5 | 0.5 |
| Dextrin palmitate | 1 | 1 | 5 | 7.5 |
| Trimethyl siloxysilicate | 0.4 | 2 | 3 | 5 |
| Polyoxybutylene polyoxypropylene glycol | 2.5 | 2.5 | 2.5 | 2.5 |
| Isopropyl myristate | 3 | 3 | 3 | 3 |
| Octocrylene | 3 | 3 | 3 | 3 |
| 2-Ethylhexyl paramethoxycinnamate | 8 | 8 | 8 | 8 |
| 2,4-Bis-[{4-(2-ethylhexyloxy)-2-hydroxy}-phenyl]-6-(4-methoxyphenyl)-1,3,5-triazine | 1 | 1 | 1 | 1 |
| Diethylamino hydroxybenzoyl hexyl benzoate | 1 | 1 | 1 | 1 |
| Dimethicone-coated fine-particle zinc oxide | 10 | 10 | 10 | 10 |
| Methyl siloxane network polymer | 5 | 5 | — | — |
| Talc | 5 | 5 | 10 | 10 |
| Purified water | 10 | 10 | 10 | 10 |
| Trisodium edetate | q.s. | q.s. | q.s. | q.s. |
| Glycerin | 1 | 1 | 1 | 1 |
| Xylitol | 1 | 1 | 1 | 1 |
| Ethanol | 10 | 10 | 10 | 10 |
| Total | 100 | 100 | 100 | 100 |
| [(A) + (B)]/(C) weight ratio | 0.091 | 0.091 | 0.333 | 0.485 |
| Abs integral value before immersion | 142.9 | 157.8 | 161.3 | 171.6 |
| Abs integral value after immersion | 157.6 | 189.7 | 181.4 | 193.1 |
| Abs change (%) before/after immersion | 110.3 | 120.2 | 112.4 | 112.5 |

As shown in Table 7, the ultraviolet ray protection effects after exposure to water increased compared to the effects before exposure to water when the weight ratio [(A)+(B)]/(C) was within the range of the present invention, even if the blended amount of component (B) was changed. This increase in absorbance shows that the coated film was not lost due to perspiration and water, and that the uniformity of the coated film was improved.

sure to water was measured. The percentages by which the diffusively reflected light increased due to exposure to water were determined from the diffusively reflected light amounts before/after exposure to water, using the following equation:

Diffusively reflected light increase percentage(%)= (Diffusively reflected light amount after water exposure)/(Diffusively reflected light amount before water exposure)×100

TABLE 8

| | Prod. Ex. 39 | Prod. Ex. 40 | Prod. Ex. 41 | Prod. Ex. 42 | Prod. Ex. 43 | Prod. Ex. 44 |
|---|---|---|---|---|---|---|
| Dimethicone | 21 | 21 | 21 | 21 | 21 | 21 |
| Isododecane | 5 | 5 | 5 | 5 | 5 | 5 |
| PPG-17 | 1 | 1 | 1 | 1 | 1 | 1 |
| PEG-9 polydimethylsiloxyethyl dimethicone | 1 | 1 | 1 | 1 | 1 | 1 |
| Isostearic acid | 0.5 | 0.5 | 0.5 | 0.5 | 0.5 | 0.5 |
| Trifluoroalkyl dimethyl trimethylsiloxysilicate | 3 | 3 | 3 | 3 | 3 | 3 |
| Ethylhexyl methoxycinnamate | 8 | 8 | 8 | 8 | 8 | 8 |
| Octocrylene | 2 | 2 | 2 | 2 | 2 | 2 |
| Dextrin palmitate | | 1 | 1 | 1 | 1 | 1 |
| Diisopropyl sebacate | 5 | 5 | 5 | 5 | 5 | 5 |
| Bis-ethylhexyloxyphenol methoxyphenyl triazine | 1 | 1 | 1 | 1 | 1 | 1 |
| Diethylamino hydroxybenzoyl hexyl benzoate | 1 | 1 | 1 | 1 | 1 | 1 |
| Distearylammonium hectorite | | 0.5 | 0.5 | 0.5 | 0.5 | 0.5 |
| Titanium oxide | 2 | 2 | 2 | 2 | 2 | 2 |
| Zinc oxide | 10 | 10 | 10 | 10 | 10 | 10 |
| (Vinyl dimethicone/methicone silsesquioxane) crosspolymer | 3 | 3 | 3 | 3 | 3 | 3 |
| Talc | 3 | 3 | 3 | 3 | 3 | 3 |
| Poly(methyl methacrylate) | 3 | 3 | 3 | 3 | 3 | 3 |
| Iron oxide | 0.5 | 0.5 | 0.5 | 0.5 | 0.5 | 0.5 |
| Titanium oxide | 4 | 4 | 4 | 4 | 4 | 4 |
| White pearl (mica/titanium oxide) interference color green (15-30 μm) | | 1 | | | | |
| White pearl (mica/titanium oxide) interference color red (15-30 μm) | | | 1 | | | |
| White pearl (mica/titanium oxide) interference color blue (15-30 μm) | | | | 1 | | |
| White pearl (mica/titanium oxide) interference color yellow (15-30 μm) | | | | | 1 | |
| White pearl (mica/titanium oxide) interference color yellow (15 μm or less) | | | | | | |
| White pearl (mica/titanium oxide) interference color yellow (70-100 μm) | | | | | | |
| White pearl (borosilicate/titanium oxide) interference color yellow (70-100 μm) | | | | | | |
| White pearl (borosilicate/titanium oxide) interference color red (100 μm or more) | | | | | | |
| White pearl (mica/titanium oxide) interference color red (15 μm or less) | | | | | | |
| White pearl (mica/titanium oxide) interference color red (15-30 μm) | 1 | | | | | |
| EDTA-3Na | 0.1 | 0.1 | 0.1 | 0.1 | 0.1 | 0.1 |
| Butylene glycol | 3 | 3 | 3 | 3 | 3 | 3 |
| Ethanol | 10 | 10 | 10 | 10 | 10 | 10 |
| Water | bal | bal | bal | bal | bal | bal |
| [(A) + (B)]/(C) weight ratio (%) | 0.000 | 0.097 | 0.097 | 0.097 | 0.097 | 0.097 |
| Diffusively reflected light increase (%) by water | 80 | 99 | 105 | 105 | 128 | 110 |

TABLE 9

| | Prod. Ex. 45 | Prod. Ex. 46 | Prod. Ex. 47 | Prod. Ex. 48 | Prod. Ex. 49 | Prod. Ex. 50 |
|---|---|---|---|---|---|---|
| Dimethicone | 21 | 21 | 21 | 21 | 21 | 21 |
| Isododecane | 5 | 5 | 5 | 5 | 5 | 5 |
| PPG-17 | 1 | 1 | 1 | 1 | 1 | 1 |
| PEG-9 polydimethylsiloxyethyl dimethicone | 1 | 1 | 1 | 1 | 1 | 1 |
| Isostearic acid | 0.5 | 0.5 | 0.5 | 0.5 | 0.5 | 0.5 |
| Trifluoroalkyl dimethyl trimethylsiloxysilicate | 3 | 3 | 3 | 3 | 3 | 3 |
| Ethylhexyl methoxycinnamate | 8 | 8 | 8 | 8 | 8 | 8 |
| Octocrylene | 2 | 2 | 2 | 2 | 2 | 2 |
| Dextrin palmitate | 1 | 1 | 1 | 1 | 1 | 1 |

TABLE 9-continued

| | Prod. Ex. 45 | Prod. Ex. 46 | Prod. Ex. 47 | Prod. Ex. 48 | Prod. Ex. 49 | Prod. Ex. 50 |
|---|---|---|---|---|---|---|
| Diisopropyl sebacate | 5 | 5 | 5 | 5 | 5 | 5 |
| Bis-ethylhexyloxyphenol methoxyphenyl triazine | 1 | 1 | 1 | 1 | 1 | 1 |
| Diethylamino hydroxybenzoyl hexyl benzoate | 1 | 1 | 1 | 1 | 1 | 1 |
| Distearylammonium hectorite | 0.5 | 0.5 | 0.5 | 0.5 | 0.5 | 0.5 |
| Titanium oxide | 2 | 2 | 2 | 2 | 2 | 2 |
| Zinc oxide | 10 | 10 | 10 | 10 | 10 | 10 |
| (Vinyl dimethicone/methicone silsesquioxane) crosspolymer | 3 | 3 | 3 | 3 | 3 | 3 |
| Talc | 3 | 3 | 3 | 3 | 3 | 3 |
| Poly(methyl methacrylate) | 3 | 3 | 3 | 3 | 3 | 3 |
| Iron oxide | 0.5 | 0.5 | 0.5 | 0.5 | 0.5 | 0.5 |
| Titanium oxide | 4 | 4 | 4 | 4 | 4 | 4 |
| White pearl (mica/titanium oxide) interference color green (15-30 μm) | | | | | | |
| White pearl (mica/titanium oxide) interference color red (15-30 μm) | | | | | | |
| White pearl (mica/titanium oxide) interference color blue (15-30 μm) | | | | | | |
| White pearl (mica/titanium oxide) interference color yellow (15-30 μm) | | | | | | |
| White pearl (mica/titanium oxide) interference color yellow (15 μm or less) | 1 | | | | | |
| White pearl (mica/titanium oxide) interference color yellow (70-100 μm) | | 1 | | | | |
| White pearl (borosilicate/titanium oxide) interference color yellow (70-100 μm) | | | 1 | | | |
| White pearl (borosilicate/titanium oxide) interference color red (100 μm or more) | | | | 1 | | |
| White pearl (mica/titanium oxide) interference color red (15 μm or less) | | | | | 1 | |
| White pearl (mica/titanium oxide) interference color red (15-30 μm) | | | | | | 1 |
| EDTA-3Na | 0.1 | 0.1 | 0.1 | 0.1 | 0.1 | 0.1 |
| Butylene glycol | 3 | 3 | 3 | 3 | 3 | 3 |
| Ethanol | 10 | 10 | 10 | 10 | 10 | 10 |
| Water | bal | bal | bal | bal | bal | bal |
| [(A) + (B)]/(C) weight ratio (%) | 0.097 | 0.097 | 0.097 | 0.097 | 0.097 | 0.097 |
| Diffusively reflected light increase (%) by water | 119 | 110 | 128 | 138 | 175 | 125 |

As shown in Tables 8 and 9, the diffusively reflected light amount after exposure to water decreased compared to the value before exposure to water, for the cosmetic (Production Example 39) not containing components corresponding to the organically modified clay mineral (component (A)) and the oil phase thickener (component (B)), and having a weight ratio [(A)+(B)]/(C) less than 0.04.

In contrast therewith, in the cosmetics (Production Examples 40 to 50) in which the weight ratio [(A)+(B)]/(C) is at least 0.04 and less than 0.68, there was no change in the diffusively reflected light amount after exposure to water, or an increase was observed. In particular, exposure to water caused the diffusively reflected light amount to increase for all of the cases (Production Examples 41 to 50) in which a pearl pigment was blended as the colorant (component (E)).

Production Examples 51 to 56

Makeup cosmetics having the compositions shown in the following Table 10 were prepared, and the color differences ΔE before/after exposure to water were measured under in vitro or in vivo conditions.

Regarding the in vitro conditions, BioSkin® #420 (0.5 g pigment) was coated with 2 mg/cm² of the samples, and a non-contact imaging colorimeter was used to measure the L-value, a-value and b-value before exposure to water and the L-value, a-value and b-value after exposure to water. The color differences ΔE before/after exposure to water were determined from the values measured before and after exposure to water, by using the following equation:

$$\text{Color difference } \Delta E [(L_{before\ immersion} - L_{after\ immersion})^2 + (a_{before\ immersion} - a_{after\ immersion})^2 + (b_{before\ immersion} - b_{after\ immersion})^2]^{1/2}$$

On the other hand, regarding the in vivo conditions, the color differences ΔE before/after exposure to water (immersion) were determined by means of the same method as the in vitro conditions other than the fact that the samples were applied directly to the skin.

TABLE 10

|  | Prod. Ex. 51 | Prod. Ex. 52 | Prod. Ex. 53 | Prod. Ex. 54 | Prod. Ex. 55 | Prod. Ex. 56 |
| --- | --- | --- | --- | --- | --- | --- |
| Dimethicone | 21 | 21 | 21 | 21 | 21 | 21 |
| Isododecane | 5 | 5 | 5 | 5 | 5 | 5 |
| PPG-17 | 1 | 1 | 1 | 1 | 1 | 1 |
| PEG-9 polydimethylsiloxyethyl dimethicone | 1 | 1 | 1 | 1 | 1 | 1 |
| Isostearic acid | 0.5 | 0.5 | 0.5 | 0.5 | 0.5 | 0.5 |
| Trifluoroalkyl dimethyl trimethylsiloxysilicate | 3 | 3 | 3 | 3 | 3 | 3 |
| Ethylhexyl methoxycinnamate | 8 | 8 | 8 | 8 | 8 | 8 |
| Octocrylene | 2 | 2 | 2 | 2 | 2 | 2 |
| Dextrin palmitate |  | 1 | 1 | 1 |  | 1 |
| Diisopropyl sebacate | 5 | 5 | 5 | 5 | 5 | 5 |
| Bis-ethylhexyloxyphenol methoxyphenyl triazine | 1 | 1 | 1 | 1 | 1 | 1 |
| Diethylamino hydroxybenzoyl hexyl benzoate | 1 | 1 | 1 | 1 | 1 | 1 |
| Disteardimonium hectorite |  | 0.5 | 0.5 | 0.5 |  | 0.5 |
| Titanium oxide (particle size 100 nm or less) | 2 | 2 | 2 | 2 | 2 | 2 |
| Zinc oxide | 10 | 10 | 10 | 10 | 10 | 10 |
| (Vinyl dimethicone/methicone silsesquioxane) crosspolymer | 3 | 3 | 3 | 3 | 3 | 3 |
| Talc | 3 | 3 | 3 | 3 | 3 | 3 |
| Poly(methyl methacrylate) | 3 | 3 | 3 | 3 | 3 | 3 |
| Iron oxide | 0.5 |  | 0.5 | 1 | 0.5 | 0.5 |
| Titanium oxide (particle size 100 nm or more) | 4 | 4 | 4 | 4 | 4 | 4 |
| White pearl (mica/titanium oxide) interference color red (15-30 μm) | 1 | 1 | 1 | 1 | 1 | 1 |
| EDTA-3Na | 0.1 | 0.1 | 0.1 | 0.1 | 0.1 | 0.1 |
| Butylene glycol | 3 | 3 | 3 | 3 | 3 | 3 |
| Ethanol | 10 | 10 | 10 | 10 | 10 | 10 |
| Water | bal | bal | bal | bal | bal | bal |
| [(A) + (B)]/(C) weight ratio (%) | 0.000 | 0.097 | 0.097 | 0.097 | 0.000 | 0.097 |
| Conditions | in vitro | | | | in vivo | |
| Before water a-value | 6.7 | 4.7 | 6.2 | 8.6 | 8.3 | 9.19 |
| b-value | 21.3 | 7.8 | 20.7 | 28.1 | 23.5 | 23.39 |
| After water a-value | 5.9 | 4.8 | 6.2 | 8.6 | 10 | 9.23 |
| b-value | 19.7 | 7.6 | 20.8 | 28.6 | 27.8 | 25.12 |
| Δa | −0.8 | 0.1 | 0 | 0 | 1.7 | 0.04 |
| Δb | −1.6 | −0.2 | 0.1 | 0.5 | 4.3 | 1.73 |
| ΔE before/after immersion | 2.54 | 0.73 | 0.81 | 0.71 | 4.78 | 1.73 |

As shown in Table 10, in cosmetics (Production Examples 51 and 55) in which the weight ratio [(A)+(B)]/(C) was less than 0.04, the color difference ΔE before/after exposure to water was large under both in vitro and in vivo conditions.

In contrast therewith, in cosmetics (Production Examples 52 to 54 and 56) in which the weight ratio [(A)+(B)]/(C) was at least 0.04 and less than 0.68, the color difference ΔE before/after exposure to water (immersion) was small.

Production Examples 57 to 59

One-day type hair dye cosmetics having the compositions shown in the following Table 11 were prepared. Strands of grey hair were dyed with the samples, and the a-values and b-values before/after exposure to water were investigated by using a non-contact imaging colorimeter. Furthermore, the apparent color development and the color uniformity were compared with those before exposure to water.

Evaluation Criteria

A: The conditions were felt to have improved compared to the conditions before exposure to water.
B: The conditions were felt to be slightly worse than the conditions before exposure to water.
C: The conditions were felt to be clearly worse than the conditions before exposure to water.

TABLE 11

|  | Prod. Ex. 57 | Prod. Ex. 58 | Prod. Ex. 59 |
| --- | --- | --- | --- |
| Isohexadecane | 12 | 19.95 | 9.95 |
| Ethylhexyl methoxycinnamate | 5 | 5 | 5 |
| Diisopropyl sebacate | 5 | 5 | 5 |
| Dextrin palmitate |  | 1 | 1 |
| Isostearic acid | 0.45 | 0.45 | 0.45 |
| Isopropyl myristate | 5 | 5 | 5 |
| PEG-9 polydimethylsiloxyethyl dimethicone | 1.5 | 1.5 | 1.5 |
| Trimethyl siloxysilicate | 5 | 5 | 15 |
| Disteardimonium hectorite |  | 0.5 | 0.5 |
| Dimethicone | 3.5 | 3.5 | 3.5 |
| n-Octylsilylated black iron oxide | 15 | 15 | 15 |
| n-Octylsilylated yellow iron oxide | 3 | 3 | 3 |
| n-Octylsilylated red iron oxide | 2 | 2 | 2 |
| Titanium oxide | 10 | 10 | 10 |
| Glycerin | 1 | 1 | 1 |
| Alcohol | 10 | 10 | 10 |
| Purified water | bal | bal | bal |
| [(A) + (B)]/(C) weight ratio (%) | 0.000 | 0.097 | 0.097 |
| Before immersion a-value | 1.6 | 1.6 | 1.7 |
| b-value | 2.4 | 2.4 | 2.3 |
| After immersion a-value | 1.5 | 1.5 | 1.7 |
| b-value | 2.2 | 2.8 | 2.7 |
| Δb before/after immersion | −0.2 | 0.4 | 0.4 |

TABLE 11-continued

|  | Prod. Ex. 57 | Prod. Ex. 58 | Prod. Ex. 59 |
|---|---|---|---|
| Apparent color development (compared to before immersion) | B | A | A |
| Apparent color uniformity (compared to before immersion) | B | A | A |

As shown in Table 11, in a cosmetic (Production Example 57) in which the weight ratio [(A)+(B)]/(C) was less than 0.04, the b-value was lower than the value before exposure to water, and in terms of the appearance, it was felt that the color development and color uniformity were worse. In contrast therewith, in cosmetics (Production Examples 58 and 59) in which the weight ratio [(A)+(B)]/(C) was at least 0.04 and less than 0.68, the b-value increased compared to the value before exposure to water, and in terms of the appearance, it was felt that the color development and color uniformity improved compared to the conditions before exposure to water.

Herebelow, formulation examples of the water-in-oil type emulsified cosmetic of the present invention will be presented. Needless to say, the present invention is not to be construed as being limited by these formulation examples in any way, and is defined by the claims. The blended amounts are all expressed in % by mass relative to the mass of the entire water-in-oil type emulsified cosmetic.

| (Component) | Blended amount (% by mass) |
|---|---|
| Formulation Example 1: BB Cream | |
| Purified water | bal (balance) |
| Decamethyltetrasiloxane | 20 |
| Trimethyl siloxysilicate | 10 |
| PEG-9 polydimethylsiloxyethyl dimethicone | 1 |
| Bis-butyl dimethicone polygyceryl-3 | 1 |
| Isostearic acid | 1 |
| Ethylhexyl methoxycinnamate | 5 |
| Isopropyl myristate | 3 |
| Dextrin palmitate | 2 |
| Titanium oxide | 24 |
| n-Octylsilylated black iron oxide | 0.5 |
| n-Octylsilylated yellow iron oxide | 1 |
| n-Octylsilylated red iron oxide | 1 |
| Titanated mica | 3 |
| Black iron oxide-coated titanated mica | 1 |
| Poly(methyl methacrylate) | 5 |
| Methylsiloxane network polymer | 2 |
| Distearyldimonium hectorite | 1 |
| Trisodium edetate | 0.3 |
| Sorbitol | 1 |
| Alcohol | 10 |
| Formulation Example 2: Body lotion | |
| Purified water | bal (balance) |
| Decamethyltetrasiloxane | 10 |
| Trimethyl siloxysilicate | 3 |
| Lauryl PEG-9 polydimethylsiloxyethyl dimethicone | 5 |
| Isostearic acid | 1 |
| Ethylhexyl methoxycinnamate | 8 |
| Homosalate | 5 |
| Octyl salicylate | 3 |
| 4-Tert-butyl-4'-methoxydibenzoylmethane | 2 |
| Isopropyl myristate | 3 |
| Dextrin palmitate | 2 |
| Hydrogenated palm oil | 2 |
| Titanated mica | 2 |
| Black iron oxide-coated titanated mica | 1 |
| Poly(methyl methacrylate) | 3 |
| Methylsiloxane network polymer | 2 |
| Disteardimonium hectorite | 0.3 |
| Trisodium edetate | 0.3 |
| Glycerin | 1 |
| Alcohol | 10 |

The invention claimed is:

1. A water-in-oil emulsified cosmetic, comprising:
   (A) 0.4 to 1% by mass, relative to the cosmetic, of at least one organically modified clay mineral;
   (B) 0.4 to 8% by mass, relative to the cosmetic, of dextrin palmitate;
   (C) 3 to 30% by mass, relative to the cosmetic, of a non-volatile liquid oil other than a silicone oil, comprising one or more liquid ultraviolet ray absorbing agents;
   (D) 0.4 to 5% by mass, relative to the cosmetic, of bis-butyldimethicone polyglycerol-3; and
   (E) 0.3 to 20% by mass, relative to the cosmetic, of a particulate colorant;
   wherein the weight ratio defined by [(A)+(B)]/(C) is at least 0.045 and less than 0.5, and wherein, upon immersion in water for 30 minutes, the UV absorbance of a film of the cosmetic is 120.2% to 133.3% of the UV absorbance of said film prior to immersion.

2. The water-in-oil emulsified cosmetic, according to claim 1, wherein said (A) at least one organically modified clay mineral is dimethyldistearylammonium hectorite.

3. The water-in-oil emulsified cosmetic, according to claim 1, wherein the weight-average particle size of said (E colorant is at largest 300 μm.

4. The water-in-oil emulsified cosmetic, according to claim 1, further comprising:
   at least one of a second (A) organically modified clay mineral, and at least one of a second (B) oil phase thickener selected from the group consisting of, sucrose fatty acid esters, dextrin (palmitate/2-ethyl hexanoate), fatty acids solid at ambient temperature, and hydrogenated vegetable oils.

* * * * *